United States Patent [19]

Irazoqui et al.

[11] Patent Number: 4,787,222
[45] Date of Patent: Nov. 29, 1988

[54] COMBINATION LOCK FOR BLOOD IDENTIFICATION SYSTEM

[75] Inventors: Carlos A. Irazoqui; John G. Gorman, both of New York, N.Y.

[73] Assignee: Novatek Medical Inc., New York, N.Y.

[21] Appl. No.: 933,994

[22] Filed: Nov. 24, 1986

[51] Int. Cl.⁴ .................... E05B 65/00; E05B 37/00
[52] U.S. Cl. .......................................... 70/57; 70/167;
70/287; 70/315
[58] Field of Search ................... 70/287–289,
70/290, 24–26, 312, 286, 163–167, 57, 58,
170–171, 315–317, 422; 604/110, 408, 409;
128/630

[56] References Cited

U.S. PATENT DOCUMENTS

| 84,192 | 11/1868 | Johnson | 70/422 |
|---|---|---|---|
| 471,167 | 3/1892 | Beasley . | |
| 527,925 | 10/1894 | Bartholomew | 70/289 |
| 803,249 | 10/1905 | Smith | 70/163 |
| 912,488 | 2/1909 | Richards | 70/422 |
| 914,819 | 3/1908 | Gagnon . | |
| 1,161,151 | 11/1915 | Muscarella | 70/287 |
| 1,395,844 | 11/1921 | Lewis | 70/422 |
| 1,551,952 | 9/1925 | Hanflig | 70/26 |
| 1,566,298 | 12/1925 | Wilson | 70/26 |
| 1,982,813 | 7/1932 | Jacobi . | |
| 2,226,390 | 12/1940 | Rosevear, Jr. | 70/171 X |
| 2,499,765 | 3/1950 | MacLaren | 70/290 X |
| 2,731,166 | 1/1956 | Raphael | 70/167 X |
| 2,847,007 | 8/1958 | Fox | 604/409 X |
| 3,200,868 | 8/1965 | Strayer . | |
| 3,237,435 | 3/1966 | Paul | 70/315 X |
| 3,343,541 | 9/1967 | Bellamy, Jr. . | |
| 3,358,479 | 12/1967 | Perry | 70/287 X |
| 3,383,885 | 5/1968 | Epstein | 70/167 |
| 3,421,347 | 1/1969 | Sotory | 70/163 X |
| 3,611,761 | 10/1971 | Atkinson | 70/315 X |
| 3,691,328 | 9/1972 | Davidson | 70/315 X |
| 3,905,477 | 9/1975 | Graham . | |
| 4,164,320 | 8/1979 | Irazoqui et al. . | |
| 4,265,101 | 5/1981 | Kaplan . | |
| 4,669,288 | 6/1987 | Percebois et al. | 70/422 X |
| 4,685,317 | 8/1987 | DeWalch | 70/422 X |

FOREIGN PATENT DOCUMENTS

| 204852 | 10/1920 | Canada | 70/26 |
|---|---|---|---|
| 245376 | 1/1911 | Fed. Rep. of Germany | 70/26 |
| 291641 | 5/1914 | Fed. Rep. of Germany | 70/24 |
| 370496 | 3/1923 | Fed. Rep. of Germany | 70/26 |
| 513082 | 11/1926 | Fed. Rep. of Germany | 70/26 |
| 154336 | 9/1938 | Fed. Rep. of Germany | 70/169 |
| 1279851 | 6/1972 | United Kingdom | 70/163 |

Primary Examiner—Gary L. Smith
Assistant Examiner—Suzanne L. Dino
Attorney, Agent, or Firm—Bacon & Thomas

[57] ABSTRACT

A system is disclosed for positive identification between a patient and a blood unit to be administered to the patient incorporating a combination lock which positively prevents access to the blood unit unless its code matches that of the patient. An alphabetic code is assigned to the patient and is set into the combination lock at the time the blood unit is removed from the blood bank. Setting of the code is achieved by the technician without necessity of external tools or mechanical skill. The combination lock has several alphabetic coded indicia dials which may be set at any orientation with respect to several locking rings. Once the combination is set, a manual clamping force exerted on the structure serves to lock the indicia rings to the associated locking ring to set the code.

19 Claims, 4 Drawing Sheets

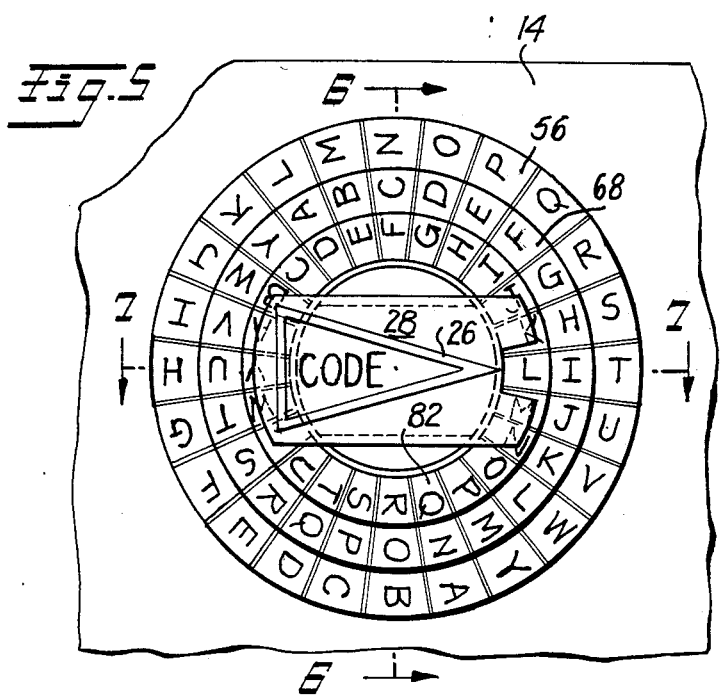
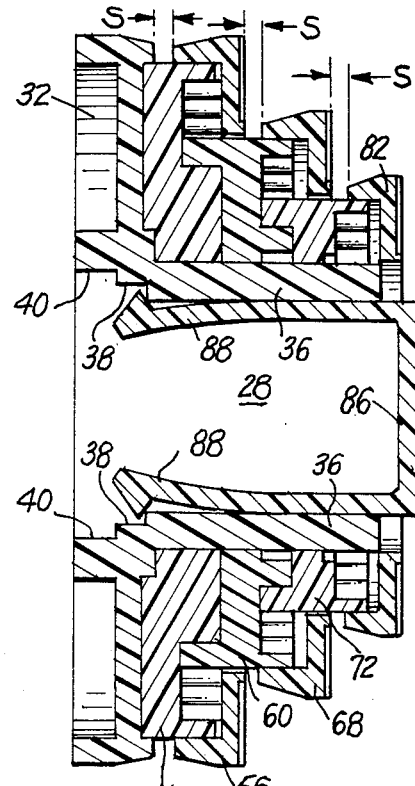
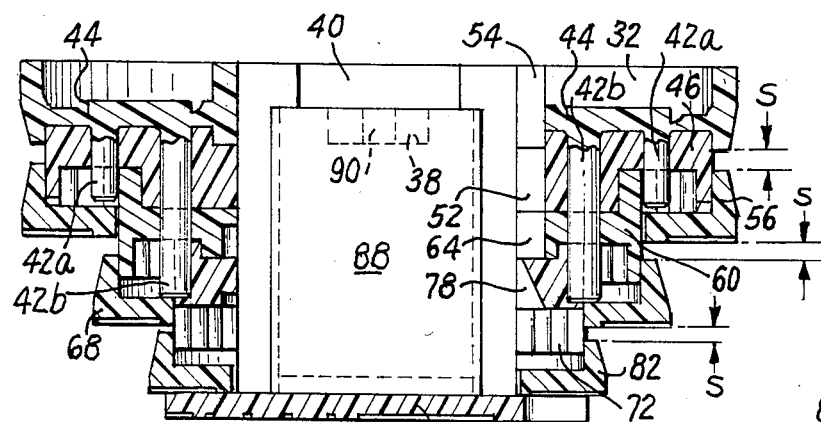
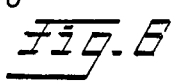
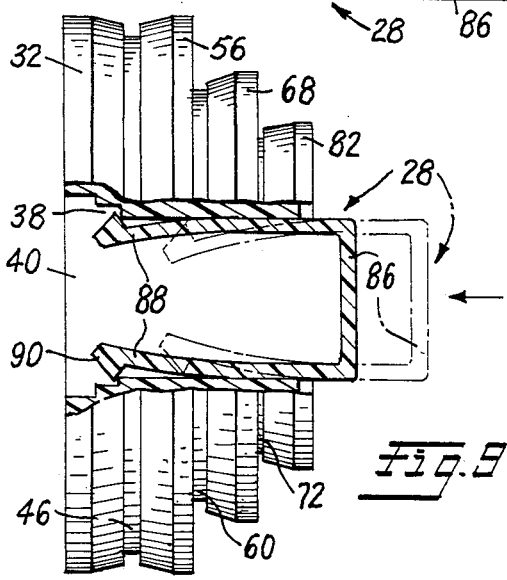
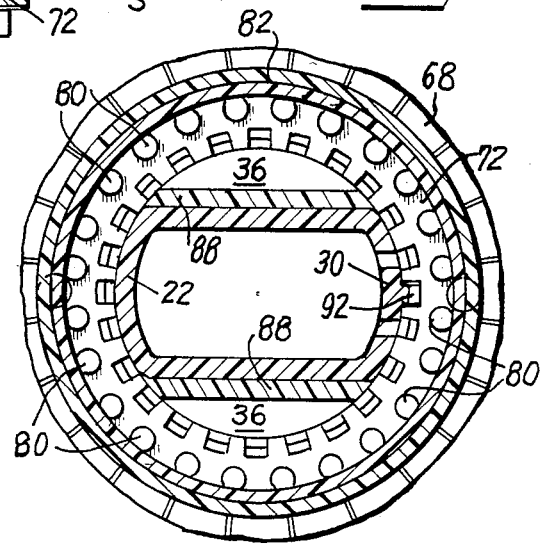

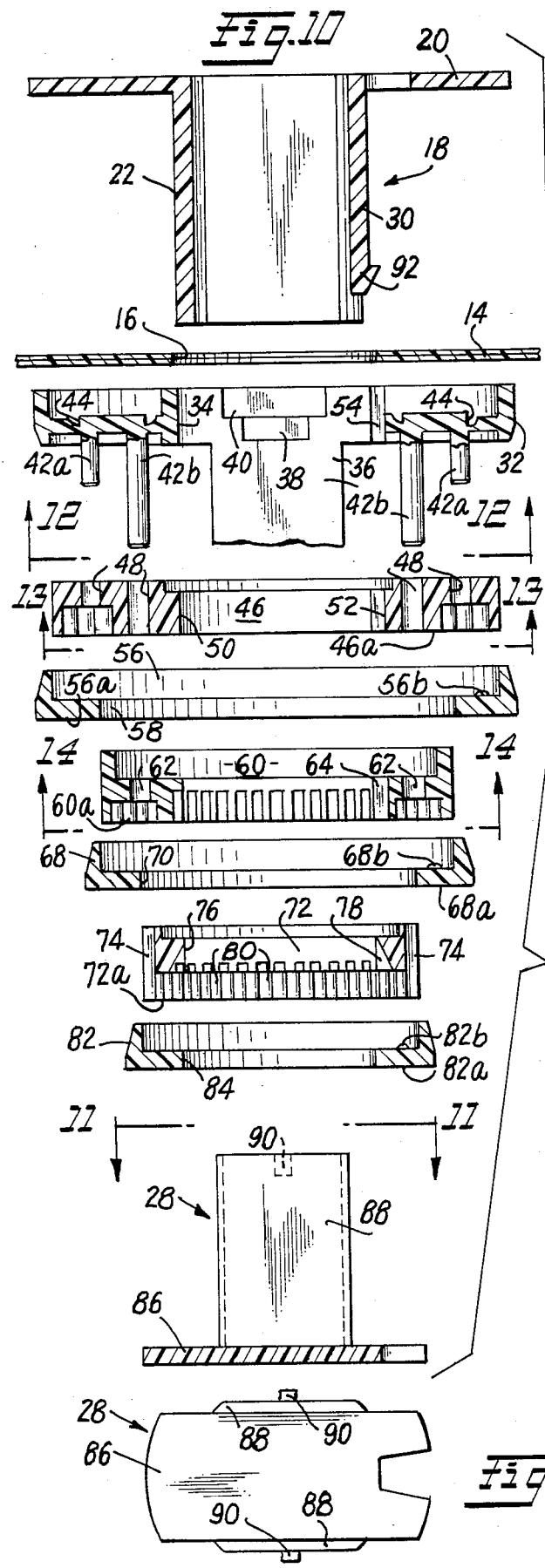

COMBINATION LOCK FOR BLOOD IDENTIFICATION SYSTEM

BACKGROUND OF THE INVENTION

The present invention relates to a system for properly identifying the patient, specimens and blood units throughout all stages of a blood transfusion sequence, starting with the patient registration at the hospital admission desk. The system ensures that the patient receives the proper type of blood unit and provides a combination lock which may be only opened with the proper code assigned to the patient.

It is well known that the technology for drawing, storing and subsequently issuing blood units to the proper patient is susceptible to human error and that an urgent need exists for improvement. In the prevention of blood transfusion errors, which may be fatal to the patient, correct identification between the patient and the blood type is of utmost importance.

In most blood transfusion systems, there are several stages where reliance must be placed upon human visual checks. Starting with the drawing of a blood specimen from a patient, through internal blood bank procedures and ending with delivery and administration of the blood unit to the patient, visual checks must be made at every step of the system to ensure the proper application of blood to the patient. Quite obviously, any system which relies upon visual checks is susceptible to human error.

Systems are known which incorporate a holder bag in which the blood unit container is stored and wherein a combination locking cap is placed over the holder bag opening. The combination on the locking cap is set to match a code given to the patient and illustrated on the patient I. D. wristband. The locking cap may not be removed unless the code properly matches that attached to the patient. The combination is set by physically removing a tab from, or inserting a peg into, either the cap or the hollow member surrounding the opening of the holder bag. A drawback to this system is that the setting of the combination requires additional tools to break the tab or insert the peg and that, once set, the combination is fixedly attached to the bag, which renders the bag unusable thereafter. Once the blood unit is used, the locking cap, along with the holder bag must be disposed of to prevent subsequent improper usage.

It is also well known to provide a flexible storage bag having means to lock an opening thereof to prevent unauthorized access to the contents of the bag. However, these systems typically incorporate a key lock structure physically attached to the bag, thereby preventing the usage of the lock with another bag structure.

SUMMARY OF THE INVENTION

The present invention provides a system for positive identification between a patient and a blood unit to be administered to the patient, and incorporates a combination lock which prevents access to the blood unit unless the proper code is set so as to enable its removal. A wristband I. D. attached to the patient incorporates an alphabetic code, which may have three letters. Each patient is assigned a different three letter code upon registration at the hospital admission desk. A blood specimen is drawn in the normal fashion and the patient's wristband code is copied onto the specimen tube label and onto any requisition forms that are necessary.

Once delivered to the registration station of the blood bank, an accesion number is assigned to the specimen tube and the patient's code letters are entered into the registration log book.

Once the specimen has been analyzed and the type of blood required has been determined, a blood unit of this type is reserved in the normal fashion. The patient's letter code does not appear on the blood bag label, which contains only the usual doner and patient information. At the dispensing station of the blood bank, the reserved blood unit is placed into an outer bag of opaque plastic material having two circular cutouts near its open top portion. The outer bag is then closed and locked by inserting the combination lock according to the invention through the circular cutouts. This lock fastens the bag opening and prevents access to the blood unit bag stored therein until its removal by setting the proper code.

The combination lock comprises a holder element, which is inserted through the circular cutouts in the outer bag, and a combination locking element which attaches to the holder element so as to grip the bag therebetween. The technologist placing the blood unit bag within the outer bag sets the combination locking element to match that in the registration log book and, by manually exerting a compressive force thereon, permanently sets the proper combination. Subsequent turning of the combination dials and snapping it onto the holder element renders the two elements positively locked together until the proper combination is set on the combination dials.

At the transfusion site, the letter code on the patient's wristband is dialed onto the combination locking element and, if the combination is proper, the combination element may be removed from the holder element so as to open the outer bag and allow access to the blood unit bag. If the improper letter code is utilized, the combination locking element will not open and inadvertent access to the blood unit bag is positively prevented.

The combination lock according to this invention is disposable and, since both the combination element and the holder element are removable from the outer bag, the outer bag may be reused a number of times. It is simple in operation, since by merely setting the combination dials and by physically forcing them together, the combination is permanently set and may not be changed. Setting the combination requires no additional tools or mechanical skill on the part of the user.

BRIEF DESCRIPTION OF THE DRAWINGS

FIG. 5 is a front view of the combination lock assembly according to the invention.

FIG. 6 is a cross-sectional view of the combination lock assembly taken along line 6—6 in FIG. 5 before the combination has been set.

FIG. 7 is a cross-sectional view of the combination lock assembly taken along line 7—7 in FIG. 5 before the combination has been set.

FIG. 8 is a cross-sectional view taken along line 8—8 in FIG. 16.

FIG. 9 is a side view, partially in section, showing the clasp member of the combination lock element assembled thereto before setting the combination.

FIG. 10 is an exploded, sectional view of the combination lock assembly according to the invention.

FIG. 11 is a rear view of the clasp member associated with the combination lock element according to the invention taken along line 11—11 in FIG. 10.

FIG. 12 is a front view of the base disk of the combination lock assembly taken along line 12—12 in FIG. 10.

FIG. 13 is a front view of the first locking ring taken along line 13—13 in FIG. 10.

FIG. 14 is a front view of the second locking ring taken along line 14—14 in FIG. 10.

DETAILED DESCRIPTION OF THE PREFERRED EMBODIMENT

Figure 1:
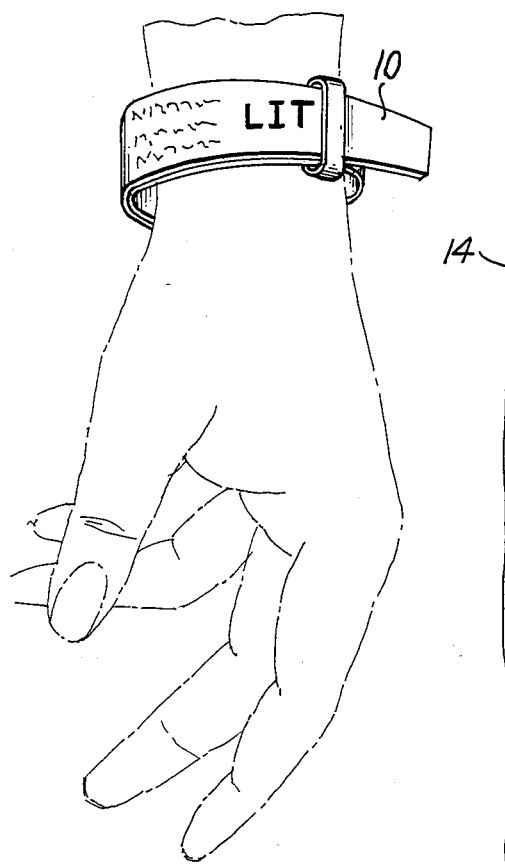
FIG. 1 is a partial, perspective view of a patient identification wristband having a three letter code according to the invention.

FIG. 1 illustrates a standard patient identification wristband 10 which is typically attached to each incoming patient in a hospital. Each I. D. wristband has a three letter code thereon, illustrated as LIT. It should be understood that, although the invention will be described in terms of a three letter combination code, codes having more or less letters or numbers may be utilized without exceeding the scope of this invention. It is anticipated that each letter position may have 24 different letters so as to allow 13,284 different three letter combinations to be utilized. The wristbands will be sequentially issued to incoming patients and, with the total number of combinations available, will provide a sufficient amount of time such that even the largest hospital will not have to utilize the same combinations.

As indicated previously, the blood specimen withdrawn from the patient will have the patient's combination code affixed thereto. Once the type of blood required by the patient has been determined, the proper type is reserved in standard, blood unit containers. The patient's code does not appear on the blood unit container.

When it is necessary to administer the blood unit to the patient, the blood unit container 12 is withdrawn from storage and placed within an outer bag 14. Outer bag 14 is formed of an opaque plastic material and has an opening along one edge such that the blood unit container 12 may be readily inserted therein. The sides of the outer bag 14 define a pair of generally cylindrical openings 16 which are aligned when the edges of the bag are brought together.

Figure 2:
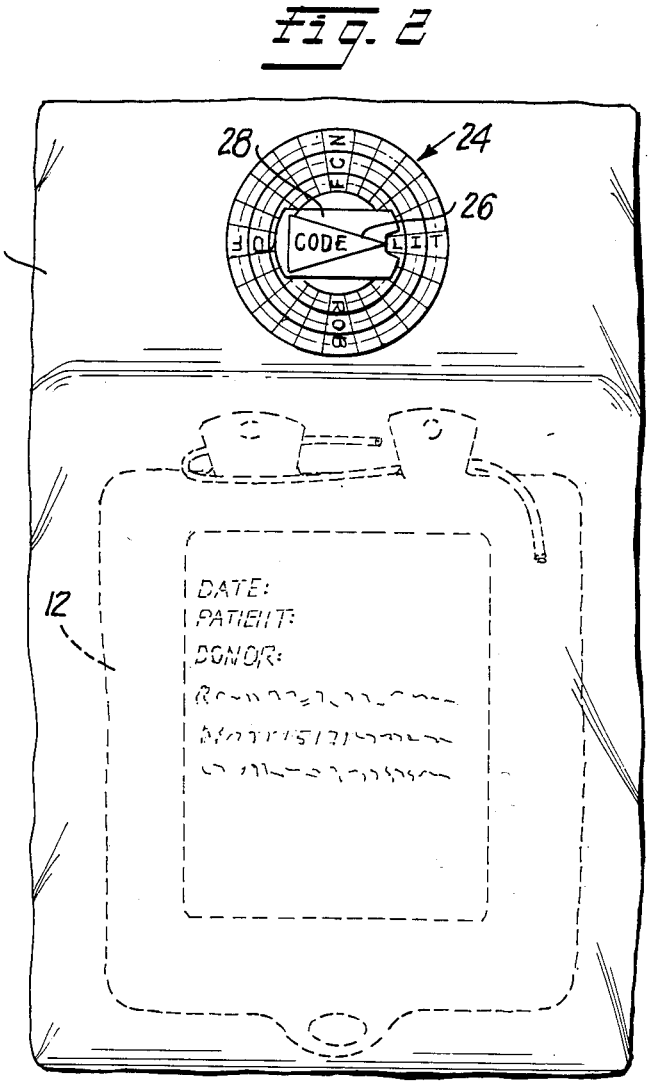
FIG. 2 is a front view of the outer bag having the combination lock attached thereto.
Figure 3:
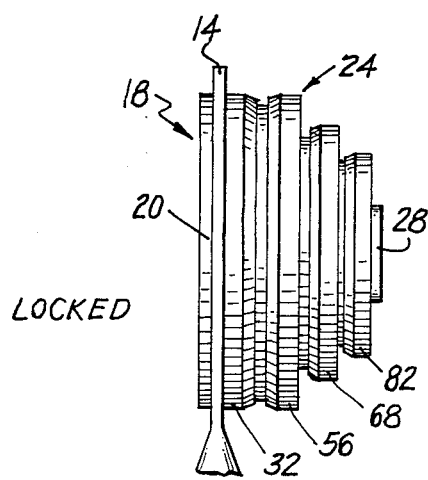
FIG. 3 is a partial side view of the outer bag with the holder element and the combination element in their locked positions.
Figure 4:
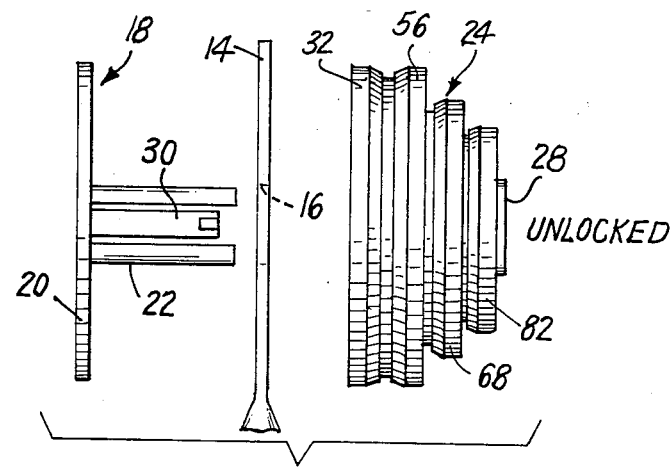
FIG. 4 is an exploded, side view showing the outer bag, the holder element and the combination element in their unlocked positions.

The open end of outer bag 14 is secured by the combination lock system according to this invention. As shown in FIG. 4, the combination lock system comprises a holder element 18, having a substantially planar portion 20 and an engaging portion 22 extending therefrom, and a combination lock assembly 24. The combination lock assembly, to be described in more detail hereinafter, has a plurality of indicia rings, in this particular instance 3 rings, each of the indicia rings having 24 letters thereon. As best seen in FIGS. 2 and 5, each of the indicia rings may be individually rotated so as to align one of the letters on its face with the arrow 26 formed on clasp member 28.

When the proper blood unit has been placed in outer bag 14, the technician ascertains the patient's letter code from the registration log book and encodes this three letter combination into the combination lock assembly 24. As will be explained in more detail hereinafter, this may be accomplished by merely aligning the proper three letters with arrow 26 and physically snapping the indicia rings against a base portion. Once the combination lock assembly 24 has been thusly encoded, holder element 18 is inserted through the cylindrical openings 16 such that portion 20 bears against one side of bag 14 while the element 22 extends through the opening. Combination lock assembly 24 is then slipped over element 22 such that flexible tab member 30 engages a corresponding slot in the combination lock assembly 24. The base portion of the combination lock assembly 24 bears against the opposite side of the bag 14 and, when the indicia rings are randomly rotated, the two elements are locked together. This positively seals the opening of opaque bag 14 such that it may be opened only when the proper combination code is set on the indicia rings.

In order to remove the blood unit container 12 from outer bag 14, it is necessary for the technician to observe the code on wristband 10 and to arrange the indicia rings in the proper coded order. If it is the proper code for the patient, combination lock assembly 24 and holder element 18 may be removed from the bag and discarded. The blood unit container 12 may then be removed, from outer bag 14 and administered to the patient in the normal fashion. Outer bag 14 may be returned to the blood bank for further usage. However, should the blood unit be incorrect, the code on the patient's wristband will not enable the combination lock assembly to be removed, thereby preventing incorrect admission of the blood unit.

The combination lock assembly 24 is shown in an exploded, cross-sectional view in FIG. 10. This assembly comprises a base member 32 of generally circular configuration, as shown in FIG. 12. Base member 32 defines a central opening 34 and has a pair of generally upstanding, diametrically opposed walls 36. The outer surfaces of walls 36 are generally curved so as to match the curvature of central opening 34. Inner surfaces of walls 36 define a first pair of diametrically opposed notches 38 and a second pair of such notches 40. Locating bosses 42a and 42b also extend generally perpendicularly from base disk 32. The opposite surface of base disk 32 defines a groove 44 extending generally adjacent the bases of locating bosses 42 so as to form an area of reduced cross-sectional thickness adjacent the bosses. This area of reduced thickness enables the locating bosses 42 to be frangibly attached to the base member 32 such that a force generated against the locating bosses 42 will cause them to break away from base member 32.

A first locking ring 46 is placed onto base member 32 such that openings 48, defined through locking ring 46, allow passage of the locating bosses 42a and 42b therethrough. Locking ring 46 also defines a central opening 50 with a locking notch 52 extending longitudinally from one side of opening 50. When locking ring 46 is assembled onto base member 32 such that locating bosses 42 extend through openings 48, locking notch 52 coincides with locking notch 54 formed in the base member 32.

The lengths of locating bosses 42a and 42b are such that locating bosses 42a do not extend beyond the surface 46a of locking ring 46 when it is assembled onto base member 32. Locking ring 46 also defines an annular recess 46b on surface 46a. The outer wall defining the recess 46b also defines a plurality of locking bosses 54 which extend generally radially inwardly into the recess 46b.

A first indicia ring 56 having the alphabetic indicia on surface 56a is placed over locking ring 46 such that it may rotate with respect thereto. Central opening 58, defined by indicia ring 56 has a diameter larger than the distance between locating bosses 42b such that they may pass through this opening and not restrict the relative rotation between the indicia ring 56 and locking ring 46.

A second locking ring of generally circular configuration whose outer diameter is less than the diameter of opening 58 is placed within opening 58 such that locating bosses 42b extend through openings 62 defined therein. Second locking ring 60 also defines a longitudinal groove 64 which is in alignment with locking grooves 52 and 54 when it is assembled onto locking bosses 42b. Annular recessed portion 60a is formed in locking ring 60 and the outer wall of the recessed portion defines a plurality of locking bosses 66.

Second indicia ring 68 is rotatably placed over second locking 60 such that it may rotate with respect thereto. Indicia ring 68 has the alphabetic indicia on surface 68a and defines a central opening 70, the diameter of which is greater than the lateral distance between locating bosses 42b. Thus, when these elements are assembled onto base member 32, indicia ring 68 may readily rotate with respect to locking ring 60 without interference from locating bosses 42b.

Third locking ring 72, of generally circular configuration, whose outer diameter is slightly less than the diameter of opening 70 is placed into indicia ring 68. Locking ring 72 defines a pair of diametrically opposite, longitudinally extending notches 74 which extend partially around locating bosses 42b so as to prevent rotation of locking ring 72 with respect to base member 32. Locking ring 72 also defines a central opening 76 and a locking notch 78. When locking ring 72 is engaged with locating bosses 42b, locking notch 78 is in longitudinal alignment with locking notches 64, 52 and 54. A recessed area in surface 72a of locking ring 72 defines a plurality of generally radially inwardly extending locating bosses 80.

Third indicia ring 82 defining central opening 84 is placed over locking ring 72 such that it may rotate with respect thereto. Indicia ring 72 has the alphabetic indicia on surface 82a.

The foregoing elements are retained in assembled relationship by clasp member 28. Clasp member 28 has a generally planar portion 86 with a pair of walls 88 extending generally perpendicular therefrom. Each of the walls 88 has a latch member 90 extending therefrom. The clasp member 28 is formed of material such that walls 88 are resiliently deformable. As can be seen in FIG. 10, clasp member 28 is inserted through all of the locking rings and indicia rings such that the exterior surfaces of walls 88 slide along the interior surfaces of walls 36 formed on base member 32. Clasp member 28 is inserted until latch elements 90 engage first notch 38, as illustrated in FIGS. 6 and 9. The lateral portions of planar portions 86 bearing against indicia ring 82 prevents the elements from becoming disassembled. While in this condition of assembly, each of the indicia rings may be rotated independently of each other and with respect to their adjacent locking rings. Thus, while the unit is assembled and may be easily handled as such, each of the indicia rings is independently manipulable.

As best seen in FIGS. 6 and 7, in this assembled condition, a certainspacing s exists between each of the indicia rings and between the base member 32 and indicia ring 56. The combination lock assembly 24 is in this assembled relationship prior to its attachment to the outer bag 14. In order to set the code, the technician merely turns each of the indicia rings such that the proper code letter is aligned with arrow 26 formed on clasp 28, as illustrated in FIG. 5. Although the indicia rings may be readily turned, each of the locking rings 46, 60 and 72, is prevented from rotating by their engagement with locating bosses 42a and 42b. Thus, the locking notches 54, 52, 64 and 78 remain in alignment.

Figure 15:
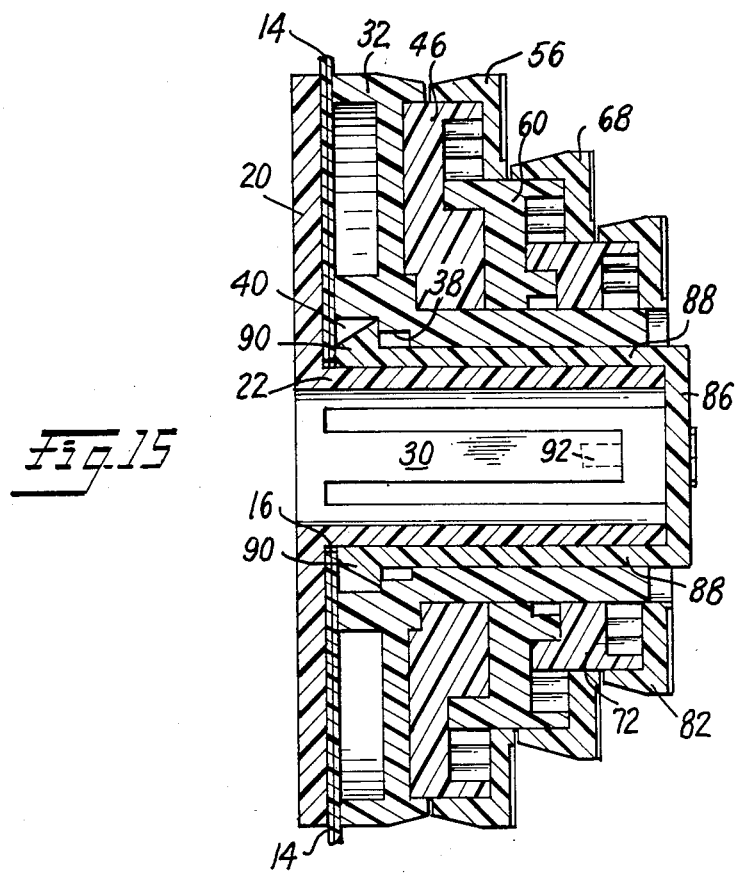
FIG. 15 is a cross-sectional view of the combination lock assembly assembled to the holder element taken along line 6—6 in FIG. 5, after setting the combination.
Figure 16:
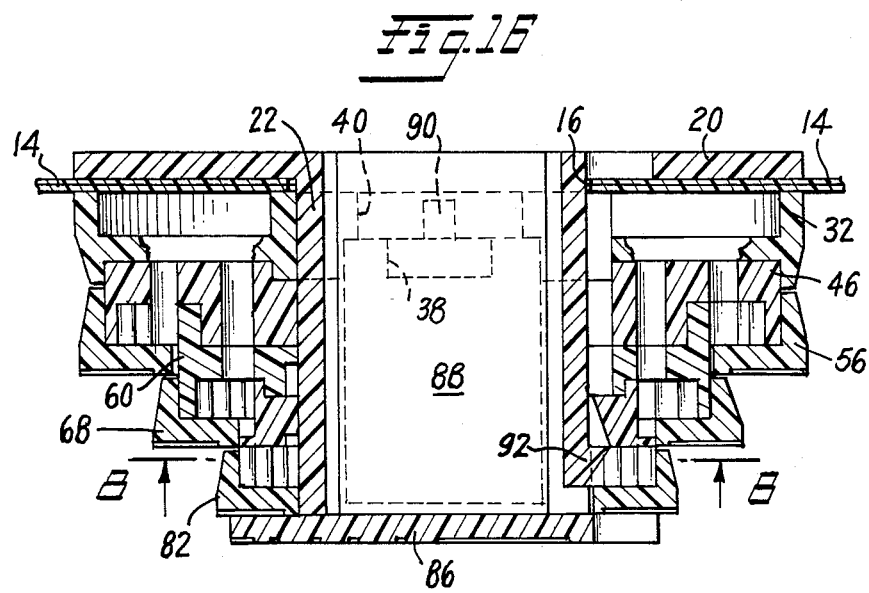
FIG. 16 is a cross-sectional view of the combination lock assembly in its assembled position taken along line 7—7 in FIG. 5.

Once the proper code has been located adjacent arrow 26, the operator need only force clasp member 28 downwardly into base member 32 until latch members 90 engage second notch 40, as shown in FIGS. 15 and 16. This downward movement causes a reduction in the space s between the adjacent elements which, in turn, causes indicia rings 68 and 56 to bear downwardly against the top of locating bosses 42b and 42a respectively. This downward force fractures the reduced thickness area of base member 32 adjacent the locating bosses and causes them to break away from the base member 32. At the same time, this downward movement of the indicia rings with respect to the adjacent locking ring serves to rotatably affix the indicia ring with its respective locking ring such that relative rotation may no longer take place. This is achieved by engagement of one or more latching bosses 56b, 68b or 82b formed on the indicia rings with locking bosses 54, 66 and 80, respectively. Once the indicia ring is forced downwardly onto the associated locking ring, the latching bosses formed on the locating ring extends between two of the locking bosses formed on the locking rings, identified as elements 54, 66 and 80. Once the code is set, the indicia rings are randomly rotated so as to misalign locking notches 54, 52, 64 and 78.

In order to attach the combination lock assembly 24 to the holder element 18, it is merely necessary to slide the assembly over engagement portion 22 extending through the outer bag 14. Latching leg 30, having a latching element 92 thereon, is resiliently deformable such that it is deformed inwardly until it snaps into locking ring 72 as illustrated in FIG. 16. Once locking element 92 is in this position, it is not possible to separate combination lock element 24 from holder element 18 unless the locking notches 78, 64, 52 and 54 are in alignment. This alignment is only achieved when the proper letter code combination is aligned with arrow 26. Thus, unless the proper code is placed on the combination lock, the elements cannot be separated and inadvertent access to the blood unit within the holder bag 14 is positively prevented.

The foregoing description is provided for illustrative purposes only and should not be construed as in any way limiting this invention, the scope of which is defined solely by the appended claims.

What is claimed is:

1. A combination lock assembly comprising:
(a) a base member;

(b) locating means frangibly attached to the base member;

(c) a plurality of locking rings mounted on the base member, each locking ring defining notch means, and engagement means to engage the locating means so as to non-rotatably mount the locking rings on the base member such that the notch means are aligned;

(d) an indicia ring associated with each locking ring;

(e) a clasp member adapted to be attached to the base member so as to retain the base member, the locking rings and the indicia rings in assembled relationship; and (f) attachment means to attach the clasp member to the base member in first and second positions such that, in the first position the indicia rings may be rotated with respect to their associated locking ring so as to align a desired indicia with the notch means to thereby set the combination and, in the second position, the locating means are detached from the base member thereby permitting the locking rings to rotate with respect to the base member.

2. The combination lock according to claim 1 further comprising means to non-rotatably affix the indicia ring to its associated locking ring when the clasp member is attached to the base member in its second position such that the indicia ring and locking ring may be rotated as a unit.

3. The combination lock according to claim 2 wherein the means to non-rotatably affix the indicia ring to its associated locking ring comprises:

(a) at least one pair of first bosses formed on the locking rings, the first bosses defining a space therebetween; and, (b) at least one second boss formed on the indicia rings such that, when the clasp member is in its second position, the second boss is located in the space between the pair of first bosses.

4. The combination lock according to claim 1 wherein the base member comprises:

(a) a generally planar, annular base portion; and (b) a pair of diametrically opposite walls extending generally perpendicular from the base portion.

5. The combination lock according to claim 4 wherein the attachment means comprises:

(a) first and second recesses defined by at least one of the walls;

(b) at least one resiliently deformable leg formed on the clasp member; and, (c) a latch element formed on the resiliently deformable leg to engage the first recess to attach the clasp member in the first position, and to engage the second recess to attach the clasp member in its second position.

6. The combination lock according to claim 5 further comprising means to non-rotatably affix the indicia ring to its associated locking ring when the clasp member is attached to the base member in its second position such that the indicia ring and locking ring may be rotated as a unit.

7. The combination lock according to claim 6 wherein the means to non-rotatably affix the indicia ring to its associated locking ring comprises:

(a) at least one pair of first bosses formed on the locking rings, the first bosses defining a space therebetween; and, (b) at least one second boss formed on the indicia rings such that, when the clasp member is in its second position, the second boss is located in the space between the pair of first bosses.

8. A coded receptacle locking system comprising:

(a) a receptacle formed of flexible material having an opening defined by opposite walls;

(b) a holder element adapted to extend through the opposite walls; and, (c) a combination lock element adapted to engage the holder element so as to grip the opposite walls therebetween wherein the combination lock element comprises:

(i) a base member;

(ii) locating means frangibly attached to the base member;

(iii) a plurality of locking rings mounted on the base member, each locking ring defining notch means and engagement means to engage the locating means so as to non-rotatably mount the locking rings on the base member such that the notch means are aligned;

(iv) an indicia ring associated with each locking ring;

(v) a clasp member adapted to be attached to the base member so as to retain the base member, the locking rings and the indicia rings in assembled relationship; and (vi) attachment means to attach the clasp member to the base member in first and second positions such that, in the first position the indicia rings may be rotated with respect to their associated locking ring so as to align a desired indicia with the notch means to thereby set the combination and, in the second position the locating means are detached from the base member thereby permitting the locking rings to rotate with respect to the base member.

9. The coded receptacle locking system according to claim 8 wherein the holder element comprises:

(a) a generally planar gripping portion;

(b) at least one resiliently deformable latching leg extending generally perpendicular from the gripping portion and adapted to extend into the combination lock element; and, (c) a first latch element formed on the latching leg so as to engage at least one of the locking rings when the notch means are out of alignment.

10. The coded receptacle locking system according to claim 9 further comprising means to non-rotatably affix the indicia ring to its associated locking ring when the clasp member is attached to the base member in its second position such that the indicia ring and locking ring may be rotated as a unit.

11. The coded receptacle locking system according to claim 10 wherein the means to non-rotatably affix the indicia ring to its associated locking ring comprises:

(a) at least one pair of first bosses formed on the locking rings, the first bosses defining a space therebetween; and, (b) at least one second boss formed on the indicia rings such that, when the clasp member is in its second position, the second boss is located in the space between the pair of first bosses.

12. The coded receptacle locking system according to claim 11 wherein the base member comprises:

(a) a generally planar, annular base position; and (b) a pair of diametrically opposite walls extending generally perpendicular to the base portion.

13. The coded receptacle locking system according to claim 12 wherein the attachment means comprises:
 (a) first and second recesses defined by at least one of the walls;
 (b) at least one resiliently deformable leg formed on the clasp member; and,
 (c) a latch element formed on the resiliently deformable leg to engage the first recess to attach the clasp member in its first position, and to engage the second recess to attach the clasp member in its second position.

14. A patient blood identification and locking system comprising:
 (a) coded indicia means attached to the patient;
 (b) an opaque receptacle formed of flexible material having an opening defined by opposite walls, the receptacle adapted to hold a blood unit bag;
 (c) a holder element adapted to extend through the opposite walls of the container;
 (d) a combination lock element having indicia thereon and adapted to engage the holder element so as to grip the opposite walls of the receptacle therebetween and thereby prevent removal of the blood unit bag wherein the combination lock element comprises:
  (i) a base member;
  (ii) locating means frangible attached to the base member;
  (iii) a plurality of locking rings mounted on the base member, each locking ring defining notch means and engagement means to engage the locating means so as to non-rotatably mount the locking rings on the base member such that the notch means are aligned;
  (iv) an indicia ring associated with each locking ring;
  (v) a clasp member adapted to be attached to the base member so as to retain the base member, the locking rings and the indicia rings in assembled relationship; and,
  (vi) attachment means to attach the clasp member to the base member in first and second positions such that, in the first position the indicia rings may be rotated with respect to their associated locking ring so as to align a desired indicia with the notch means to thereby set the combination and, in the second position the locating means are detached from the base member thereby permitting the locking rings to rotate with respect to the base member; and,
 (e) means to encode the patient's coded indicia into the combination lock element such that it will release the holder element only when its indicia matches that of the patient.

15. The patient blood identification and locking system according to claim 14 wherein the holder element comprises:
 (a) a generally planar gripping portion;
 (b) at least one resiliently deformable latching leg extending generally perpendicular from the gripping portion and adapted to extend into the combination lock element; and,
 (c) a first latch element formed on the latching leg so as to engage at least one of the locking rings when the notches are out of alignment.

16. The patient identification and locking system according to claim 15 further comprising means to non-rotatably affix the indicia ring to its associated locking ring when the clasp member is attached to the base member in its second position such that the indicia ring and locking ring may be rotated as a unit.

17. The patient blood identification and locking system according to claim 16 wherein the means to non-rotatably affix the indicia ring to its associated locking ring comprises:
 (a) at least one pair of first bosses formed on the locking rings, the first bosses defining a space therebetween; and,
 (b) at least one second boss formed on the indicia rings such that, when the clasp member is in its second position, the second boss is located in the space between the pair of first bosses.

18. The patient blood identification and locking system according to claim 17 wherein the base member comprises:
 (a) a generally planar, annular base portion; and
 (b) a pair of diametrically opposite walls extending generally perpendicular to the base portion.

19. The patient blood identification and locking system according to claim 18 wherein the attachment means comprises:
 (a) first and second recesses define by at lesat one of the walls;
 (b) at least one resiliently deformable leg formed on the clasp member; and,
 (c) a latch element formed on the resiliently deformable leg to engage the first recess to attach the clasp member in its first position, and to engage the second recess to attach the clasp member in its second position.

* * * * *